(12) United States Patent
Brodbeck et al.

(10) Patent No.: US 9,011,469 B2
(45) Date of Patent: Apr. 21, 2015

(54) DEVICE FOR PRODUCING ANASTOMOSES AND COAGULATION ELECTRODE

(75) Inventors: Achim Brodbeck, Metzingen (DE); Lothar Mitzlaff, Lagos (PT)

(73) Assignee: Erbe Elektromedizin GmbH, Tuebingen (DE)

( * ) Notice: Subject to any disclaimer, the term of this patent is extended or adjusted under 35 U.S.C. 154(b) by 1099 days.

(21) Appl. No.: 13/059,682

(22) PCT Filed: Jul. 23, 2009

(86) PCT No.: PCT/EP2009/005365
§ 371 (c)(1),
(2), (4) Date: Feb. 18, 2011

(87) PCT Pub. No.: WO2010/020328
PCT Pub. Date: Feb. 25, 2010

(65) Prior Publication Data
US 2011/0152862 A1    Jun. 23, 2011

(30) Foreign Application Priority Data

Aug. 19, 2008  (DE) .......................... 10 2008 038 313
Sep. 22, 2008  (DE) .......................... 10 2008 048 293

(51) Int. Cl.
*A61B 18/12* (2006.01)
*A61B 18/14* (2006.01)
(Continued)

(52) U.S. Cl.
CPC ............ *A61B 18/1402* (2013.01); *A61B 17/11* (2013.01); *A61B 18/1442* (2013.01); *A61B 2017/1103* (2013.01); *A61B 2017/1107* (2013.01); *A61B 2018/00184* (2013.01); *A61B 2018/00619* (2013.01)

(58) Field of Classification Search
CPC .............. A61B 17/11; A61B 18/1402; A61B 18/1442; A61B 2017/1103; A61B 2017/1107; A61B 2018/00184; A61B 2018/00619
USPC .............................................. 606/40, 49, 153
See application file for complete search history.

(56) References Cited

U.S. PATENT DOCUMENTS 3,774,615 A    11/1973  Lim et al.
5,188,638 A *  2/1993  Tzakis .......................... 606/153

(Continued)

FOREIGN PATENT DOCUMENTS

CN       1301084 C       2/2007
WO   WO 99/59486 A2    11/1999
WO   WO 03/061487 A1    7/2003

*Primary Examiner* — Joseph Stoklosa
*Assistant Examiner* — Jocelyn D Ram
(74) *Attorney, Agent, or Firm* — Dickstein Shapiro LLP

(57) ABSTRACT

A device for producing anastomoses between first and second hollow organs, each having inner and outer surfaces. The device comprises a sleeve with an electrode arrangement, over which the first hollow organ is placed such that its inner surface comes to lie on an outermost surface of the sleeve, and an outer electrode arrangement, which can be brought into electrical contact with the opposing electrode arrangement carrying the second hollow organ, which is pushed over the first hollow organ. The outer electrode arrangement comprises a plurality of lamellae, configured and arranged such that, in a closed state, the lamellae form a through aperture and the inner edges of the lamellae lie against the second hollow organ and, in an open state, a gap is formed between the lamellae through which the hollow organs connected to one another can be guided outwardly out of the through aperture.

9 Claims, 10 Drawing Sheets

(51) Int. Cl.
*A61B 17/11* (2006.01)
*A61B 18/00* (2006.01)

(56) References Cited

U.S. PATENT DOCUMENTS

| | | | |
|---|---|---|---|
| 8,303,610 B2* | 11/2012 | Schubert | 606/153 |
| 8,808,316 B2* | 8/2014 | Brodbeck | 606/153 |
| 2002/0032462 A1* | 3/2002 | Houser et al. | 606/213 |
| 2003/0114845 A1* | 6/2003 | Paton et al. | 606/40 |
| 2003/0236518 A1* | 12/2003 | Marchitto et al. | 606/27 |
| 2005/0055022 A1* | 3/2005 | Schubert | 606/49 |
| 2006/0020263 A1 | 1/2006 | Rothstein et al. | |
| 2007/0276363 A1* | 11/2007 | Patton et al. | 606/51 |
| 2009/0234347 A1* | 9/2009 | Treat et al. | 606/30 |
| 2010/0057075 A1* | 3/2010 | Marchitto et al. | 606/33 |
| 2012/0101500 A1* | 4/2012 | Winter | 606/49 |
| 2012/0116428 A1* | 5/2012 | Brodbeck | 606/153 |
| 2013/0035683 A1* | 2/2013 | Weisshaupt et al. | 606/37 |

\* cited by examiner

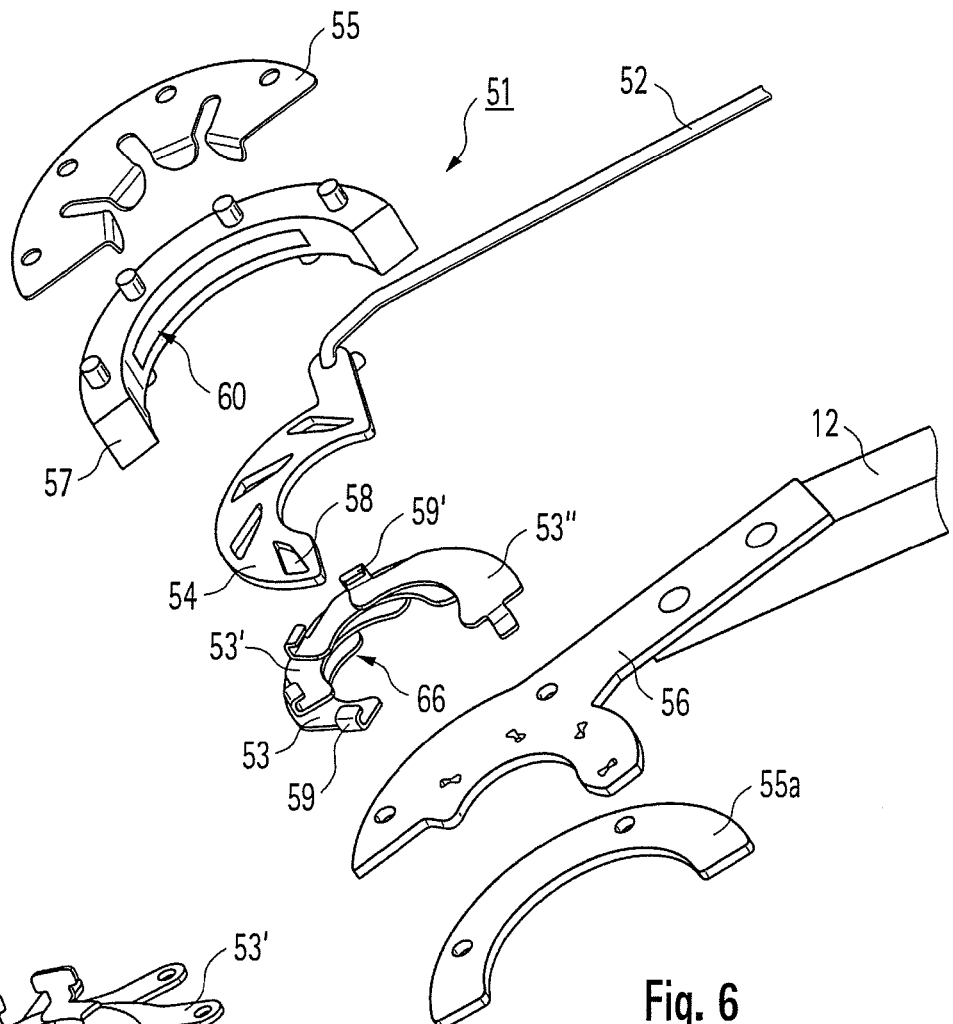
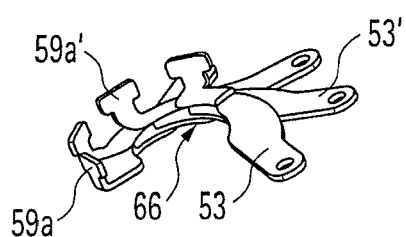
Fig. 6
Fig. 7

DEVICE FOR PRODUCING ANASTOMOSES AND COAGULATION ELECTRODE

FIELD OF THE INVENTION

Embodiments of the invention relate to a device for producing anastomoses and a coagulation electrode.

BACKGROUND

An anastomosis is a connection between two anatomical structures. For example, blood vessels severed during an organ transplantation can be connected to one another by anastomoses.

In surgery, various methods for producing such anastomoses are known. For example, the connection can be made using suturing techniques. Inserts also exist that permit an organic connection by adhesive techniques. In this context, fibrin glues are often used, which enable the very advantageous connection of organs, particularly hollow organs. However, the tolerability of such adhesives is problematic, since they can have thrombogenic and toxic properties.

Clamping techniques are also used to create a connection at a suitable site. Various aids, such as rings, cuffs or stents are used to assist in the production of anastomoses.

It is disadvantageous, however, that these aids usually remain in the hollow organ being connected and can cause rejection reactions or increase the risk of thromboses.

WO 03/061487 A1 discloses connecting hollow organs by the application of a suitable high frequency (HF) current. When the HF current is applied, biological welding of the tissue structures takes place. The cellular substance coagulates with the result that the protein structures adhere, so that a controlled, secure and rapid connection can be created. WO 03/061487 A1 provides an instrument for the application of an HF current, said instrument comprises an inner sleeve and an outer sleeve. These sleeves each comprise an electrode, which is ring-shaped, to which the HF current is supplied. This instrument is a bipolar HF instrument. To connect the ends of a blood vessel, the first end is guided through the inner sleeve and is folded over such that the tissue comes to lie against the outside of the inner sleeve. The second end of the vessel is pulled over the inner sleeve and the end section of the blood vessel situated thereon. The outer sleeve can be opened and placed over the inner sleeve and the tissue situated thereon. The electrodes are arranged on the sleeves such that the first and second ends of the vessel are clamped between the electrodes on the sleeves. On application of the HF current, said current flows through the tissue and welds the ends.

A problem with WO 03/061487 A1 lies in the fact that in order to weld or coagulate hollow organs having different diameters, a plurality of differently configured instruments is needed. In particular, the gap between the electrodes and the sleeves must be dimensioned so that it is matched to the thicknesses of the walls.

Only when the electrodes are optimally placed on the tissue structures does the advantageous welding of the tissue structures take place. The coagulation procedure requires continuous pressure on the tissue structures or vessel end sections throughout the coagulation process.

The results finally achieved with the instrument disclosed in WO 03/061487 A1 are strongly dependent on the choice of a suitable instrument, i.e. on the judgment of the treating physician and are therefore difficult to document and reproduce.

SUMMARY

Proceeding from this prior art, it is an object of the embodiments disclosed herein to provide a device for producing anastomoses between first and second hollow organs, which is simple to operate and is suitable for forming high quality anastomoses, while also avoiding the aforementioned disadvantages. A coagulation electrode suitable for this purpose is also provided.

In particular, the problem associated with the prior art is solved with a device for producing anastomoses between first and second hollow organs, each having an inner surface and an outer surface. Said device comprises a sleeve with an inner electrode arrangement, over which the first hollow organ is placed such that the inner surface thereof comes to lie on an outermost surface of the sleeve, and an outer electrode arrangement which is situated, in particular, radially opposing the inner electrode arrangement and can be brought into electrical contact with the second hollow organ, which is pushed over the first hollow organ, such that the electrode arrangements make contact with the outer surfaces of the hollow organs. The outer electrode arrangement comprises a plurality of lamellae that are movable relative to one another by means of at least one guide member and are configured and arranged movable such that, in a closed state, inner edges of the lamellae form a through aperture and lie against the second hollow organ and, in an open state, a gap is formed between the lamellae, leading from outside to the through aperture, through which the hollow organs connected to one another can be guided outwardly out of the through aperture.

An essential concept of the embodiments described herein is that the outer electrode is formed by a plurality of lamellae, which are movable relative to one another. The lamellae are arranged such that they are able to assume at least two states; specifically, a closed state and an open state. In the open state, at least the lamellae are spaced apart from the sleeve with the inner electrode arrangement such that a through aperture is formed, in which the relevant sections of the hollow organs can be positioned, preferably largely in the absence of tissue contact or radial force application. In the closed state, the inner edges of the lamellae lie at least partially on the hollow organ and enable direct application of the HF current. The outer electrode arrangement with the lamellae is partable. In the open state, a gap can form, dividing the lamellae. Due to the gap, the unconnected hollow organ or vessel can be introduced and the connected organ or vessel can be removed from the device.

Preferably, the lamellae can exert mechanical pressure on the hollow organs. The closing and coagulation conditions can be determined relatively precisely. By this, the formation of anastomoses having a high load-bearing capability can be ensured. Following connection of the hollow organs, the device can be easily removed in the open state. Injury to the organs or excessive loading of the created connection is avoided.

The lamellae can be adjustable such that, in the closed state, an aperture that matches the hollow organ to be treated is formed. Hollow organs with different dimensions can therefore be treated with a device according to the embodiments described herein. For example, blood vessels with different diameters can be treated. The instrument can be suitable for connecting veins and arteries.

The lamellae can be constructed and/or arranged in the manner of an iris diaphragm. The through aperture is therefore formed substantially circular. This is advantageous for a number of applications, such as the connection of vessels. Furthermore, an iris diaphragm is particularly suitable for providing a substantially continuous contact surface of the lamellae. A continuous application of the HF current therefore takes place. An applied mechanical pressure can be evenly distributed over the outer surface and surfaces of the second hollow organ.

The sleeve can be arranged fixed relative to the outer electrode in a holder or mounting. The sleeve is then arranged in a predetermined position relative to the outer electrode. Positioning of the sleeve relative to the outer electrode is therefore dispensable. In addition, the disclosed device can be constructed substantially more compact by fixing it in a holder. Handling is simplified by the fixed or adjustable positioning.

The mounting can be removed for individual manipulation of the sleeve. This means that the mounting can be released from the device and used separately therefrom. It is therefore possible, in a preparation phase, to arrange the first hollow organ and/or the second hollow organ in or on the sleeve. Then, the sleeve and the device can be coupled such that the sleeve is situated in an advantageous position relative to the outer electrodes. Following the coagulation procedure, it can be advantageous to release the mounting from the device again, to avoid straining the connected hollow organs unnecessarily.

In the closed state, the inner edges of the lamellae can be spaced at substantially the same distance from the sleeve. Therefore, in the closed state, the inner edges lie against the second hollow organ, particularly on the inner surface thereof. The HF current is applied directly to the tissue. The achieved connection is of correspondingly better quality.

The diameter of the through aperture is adjustable with the movement of the lamellae. The device can therefore be opened and closed by moving the lamellae.

In the open state, the gap can divide the outer electrode in two halves, which can be moved apart from one another. It is thus possible to create an iris, which can be divided, for example, into two semicircles. This facilitates the safe removal of the device following a coagulation procedure.

The sleeve can be held on an actuating device and can be configured to be dismantled into two parts such that the parts can also be brought from a closed state, forming a closed tubular section, into an open state for removal from the hollow organ. The sleeve can therefore be configured in two parts, so that said sleeve can be disassembled after or before the application of the HF current. For example, it may be possible to spread the individual parts of the sleeve apart in to ensure better handling of the organs. The spreading of the sleeve can also prevent the hollow organ placed over the sleeve from slipping off.

In a closed state, the actuating device can be pre-tensioned. The closed state therefore establishes itself automatically.

The lamellae can be pre-tensioned into the closed state with a defined force by a tensioning device. Preferably, the tensioning device can be adjusted so that, in the closed state, the lamellae are pressed with a pre-defined force against the hollow organs. This force not only enables reliable coagulation of the tissue, but is also dimensioned so that the hollow organs are not damaged. By setting the tensioning device, repeatability of the treatment results can be assured.

The problem defined above is also solved with a coagulation electrode, comprising: a mounting ring; a plurality of lamellae mounted on the mounting ring, said lamellae being pivotable from an open state to a closed state, in the manner of an iris diaphragm, to form electrode sections; a linkage ring arranged rotatable relative to the mounting ring and which engages with guide members on the lamellae such that on rotation of the linkage ring relative to the mounting ring, the lamellae are pivoted from the closed state to the open state and vice versa, wherein the mounting ring and the linkage ring are each configured in two parts such that they can be moved away from one another together with the lamellae mounted on the mounting ring and engaging with the linkage ring.

A coagulation electrode of this type has similar advantages to the aforementioned device. In particular, the coagulation electrode is partable and is therefore easily removed after application of the HF current. This means that the coagulation electrode can easily be removed from the connected hollow organ.

The linkage ring can also can also be a lamella and perform the function thereof.

The linkage ring can comprise linkage ring sections that are movable separately from one another, in particular, with guide rods.

The linkage ring can comprise exactly two linkage ring sections forming the linkage ring. The sections can actuate the lamellae. In particular, the lamellae can be rotated relative to the mounting ring (preferably comprising two mounting ring sections). The lamellae are brought into the open or closed state.

BRIEF DESCRIPTION OF THE DRAWINGS

Embodiments of the invention will now be described in greater detail with reference to the drawings, in which:

FIG. 6 shows the iris diaphragm of FIG. 5 in an exploded view;

FIG. 7 shows a further embodiment of the lamellae for an iris diaphragm;

DETAILED DESCRIPTION

In the following description, the same reference signs are used for similar and similarly acting parts.

Figure 1:
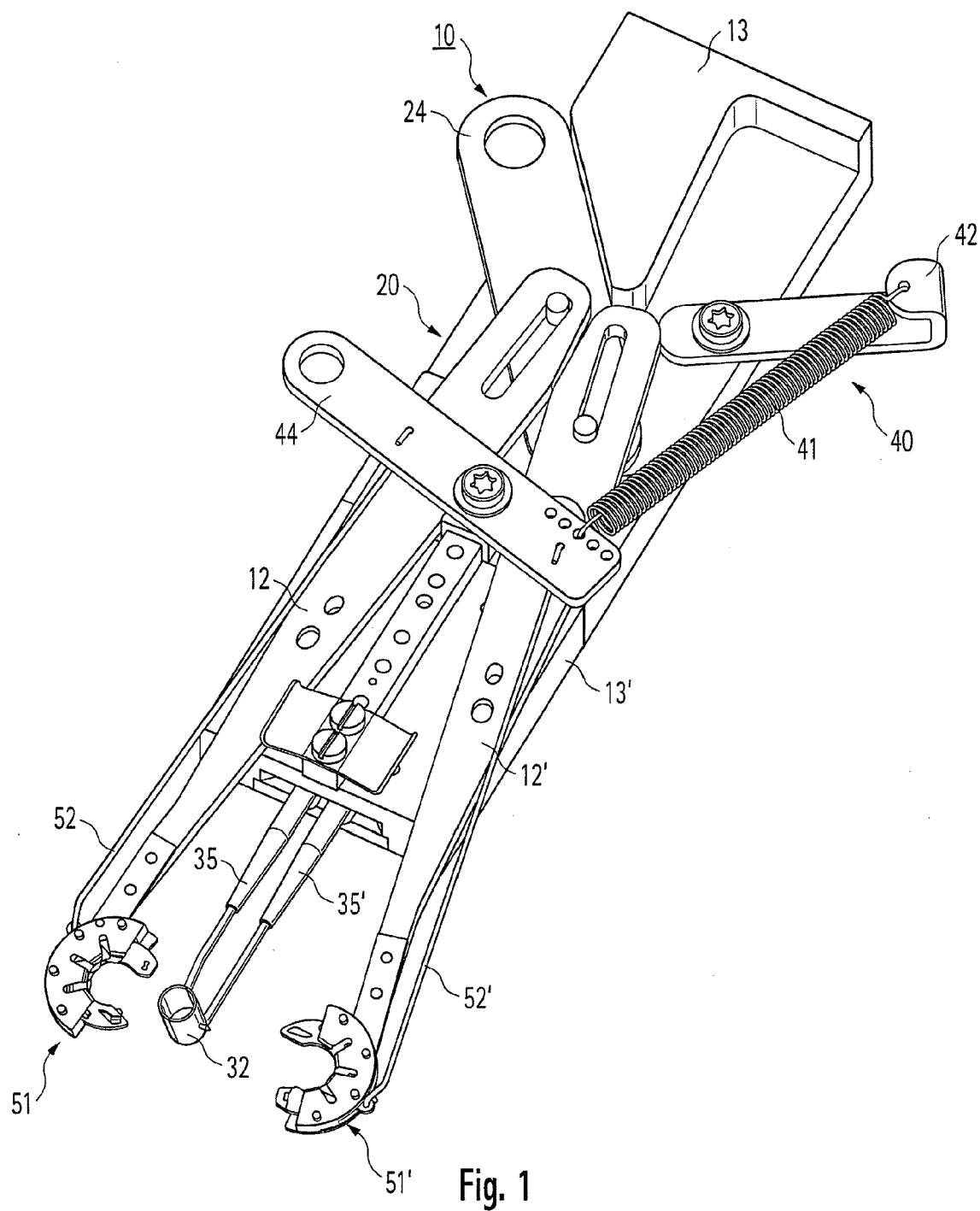
FIG. 1 shows an electrosurgical instrument for producing anastomoses, with the arms opened.

FIG. 1 shows an electrosurgical instrument 10 for producing anastomoses. The instrument 10 comprises a base plate 13, on which arms 12, 12' are pivotably mounted. A closing device 20 serves to actuate the arms 12, 12'. Said closing device 20 comprises a closure actuating element 24, which is connected to the arms 12, 12' via a linkage guide. The closure actuating element 24 has essentially two positions; specifically, a first position in which the electrosurgical instrument 10 is open and a second position in which the electrosurgical instrument 10 is closed. Preferably, the closing device 20 is configured so that the arms 12, 12' are fixed in the second position such that unintentional opening of the electrosurgical instrument 10 is not possible (see FIG. 2).

Figure 2:
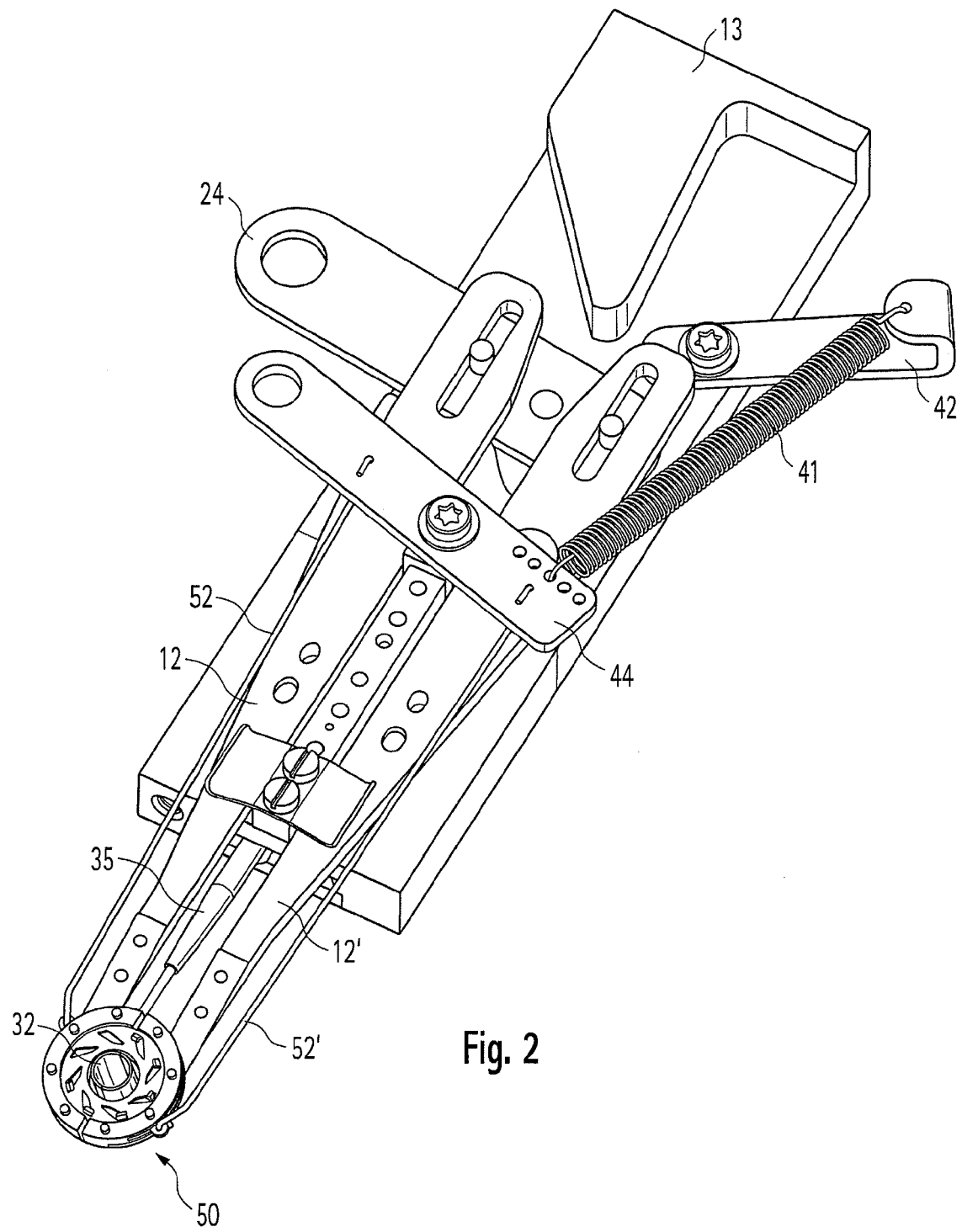
FIG. 2 shows the instrument of FIG. 1 with the arms closed (and iris diaphragm open)
Figure 3:
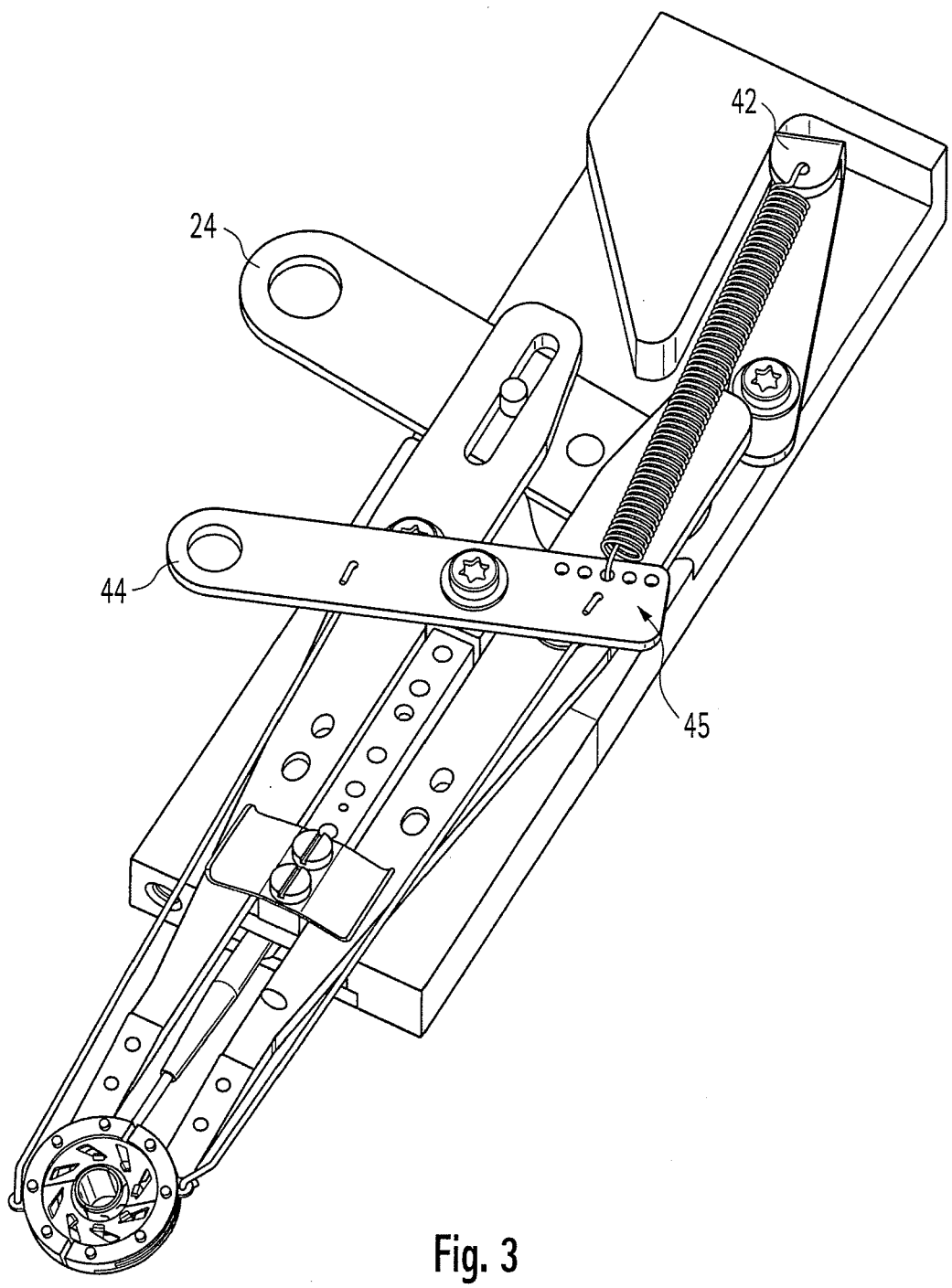
FIG. 3 shows the instrument of FIGS. 1 and 2 with the arms closed (and the iris diaphragm closed)

Situated at the distal end of the arms 12, 12' are half diaphragms 51, 51', which form an iris diaphragm 50 in the closed state of the electrosurgical instrument 10 (see FIGS. 2 and 3).

The electrosurgical instrument 10 also has a tensioning device 40 for actuating the iris diaphragm 50. Said tensioning device 40 comprises a tensioning device actuating element 42 and a force deflector 44, which are pivotably mounted on the base plate 13, a tensioning spring 41 and two actuating elements 52, 52'. The actuating elements 52, 52' extend, respectively, along the first arm 12 and the second arm 12' and transmit the forces exerted by the tensioning device 40 to the mechanisms forming the iris diaphragm 50. In the open position of the electrosurgical instrument 10, the tensioning device 40 is also in an open position (see FIG. 1). In the second, closed position of the electrosurgical instrument 10, the tensioning device 40 can be tensioned by actuating the tensioning device actuating element 42. FIG. 3 shows the tensioning device actuating element 42 in the tensioned state. On actuation of the tensioning device actuating element 42, the tensioning spring 41 which is connected to the force deflector 44 is tensioned. This results in a rotary movement of the force deflector 44 about a pivot point situated between the arms 12, 12'. The rods or actuating elements 52, 52', which are attached to the force deflector 44 substantially symmetrically about said pivot point, execute a translation movement in the proximal (actuating element 52') or the distal (actuating element 52) direction. This movement leads, as described in greater detail below, to closing and opening of the iris diaphragm 50.

It should be noted that, in the tensioned state, the tensioning spring 41 continuously exerts a force, via the actuating elements 52, 52' on the mechanisms forming the iris diaphragm 50. The value of this force can be adjusted with a closing force adjusting device 45 (see FIG. 3). The embodiment of the force deflector 44 as shown in FIG. 3 comprises a plurality of bores with different distances from the pivot point of the force deflector 44. The tensioning spring 41 is configured such that said spring can be anchored in the individual bores. The spring force of the tensioning spring 41 is therefore applied to the force deflector 44 with a different leverage depending on the position in the bores. As shown in FIGS. 1-3, the force deflector 44 extends beyond the base plate 13 such that said force deflector is manually actuatable. The iris diaphragm 50 can also be opened and closed in the non-tensioned state via the force deflector 44, which serves as an actuating element.

Figure 4:
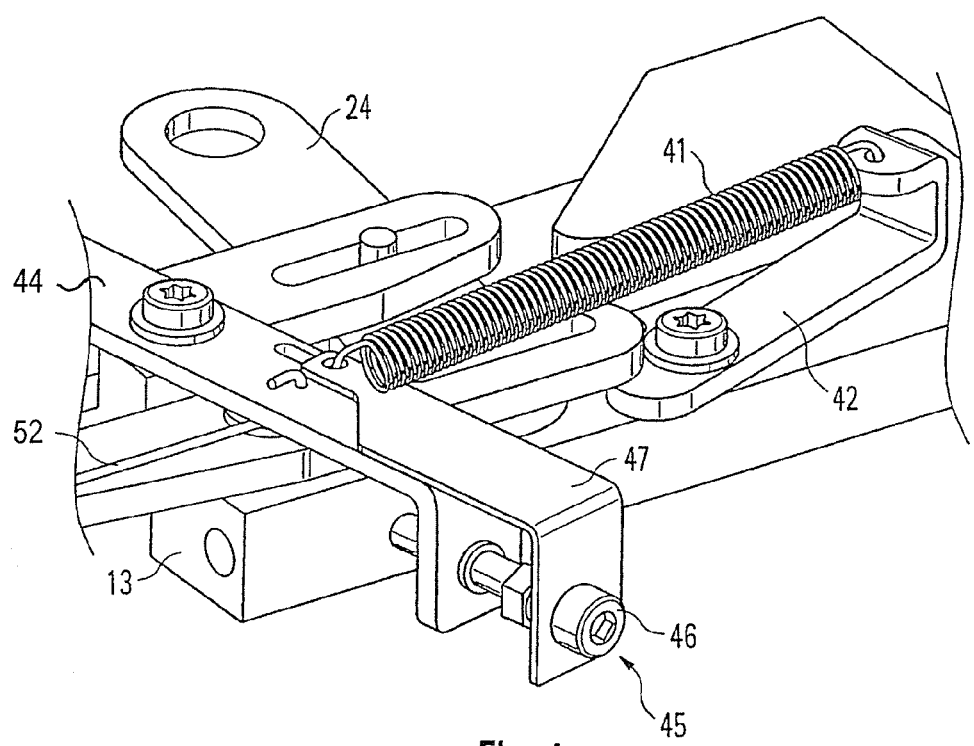
FIG. 4 shows a closing force adjusting device for the instrument of FIGS. 1 to 3.

FIG. 4 shows a further embodiment of the tensioning device 40. In this case, the closing force adjusting device 45 comprises an adjusting screw 46 and an angle bracket 47. The angle bracket 47 is fastened to the force deflector 44 such that said angle bracket can be displaced along a longitudinal axis by actuation of the adjusting screw 46. In the exemplary embodiment shown in FIG. 4, the tensioning spring 41 acts on the angle bracket 47. By actuating the adjusting screw 46, the lever with which the tensioning spring 41 exerts the force on the force deflector 44 can be adjusted in steps (i.e., stepwise adjusted).

A positioning device 30 (see FIG. 5) is another key element of the electrosurgical instrument 10. Said positioning device comprises a sleeve 32 for accommodating the hollow organs and two sleeve actuating arms 35, 35'. The positioning device 30 essentially serves to position the hollow organs in the center of the iris diaphragm 50; it also provides a sleeve electrode 36. The sleeve 32 is constructed substantially cylindrically and comprises a first sleeve section 33 and a second sleeve section 33'. In cross-section, transversely to the longitudinal axis of the sleeve 32, the sleeve sections 33, 33' each form a semicircle. The sleeve sections 33, 33' are connected to the sleeve actuating arms 35 and 35', respectively. Said actuating arms 35, 35' are pivotably fastened to a removable section 13' (FIG. 1) of the base plate 13, such that the sleeve sections 33, 33' can be opened and closed. In the closed state, the sleeve sections 33, 33' lie against one another and form the sleeve 32. The positioning device 30 can thus be opened and closed via the sleeve actuating arms 35, 35'. Preferably, a spring force which keeps the sleeve sections 33, 33' closed is applied to the sleeve actuating arms 35, 35'. The removable section 13', on which the sleeve actuating arms 35, 35' are pivotably mounted, is connected to the base plate 13 via a plug-in connection. In order to accommodate the hollow organs, the positioning device 30 can be detached from the remaining components of the electrosurgical instrument 10 and individually operated.

The partability of the sleeve 32 is particularly advantageous when placing the instrument 10 on, and removing the instrument from, the hollow organ. To facilitate this procedure, the sleeve 32 comprises at least two spikes 28, which are arranged on the sleeve sections 33, 33' radially to the longitudinal axis of the sleeve 32. If the hollow organ, or the sections thereof, is pushed over the sleeve 32, the spikes 28 fix the hollow organs or vessels that have been placed thereon. The sleeve actuating arms 35, 35' limit the advance of said organs.

Following accommodation of the hollow organs, the removable section 13' can be reconnected to the base plate 13 and brought into a position which is suitable for connecting the sections of the hollow organ.

Figure 8:
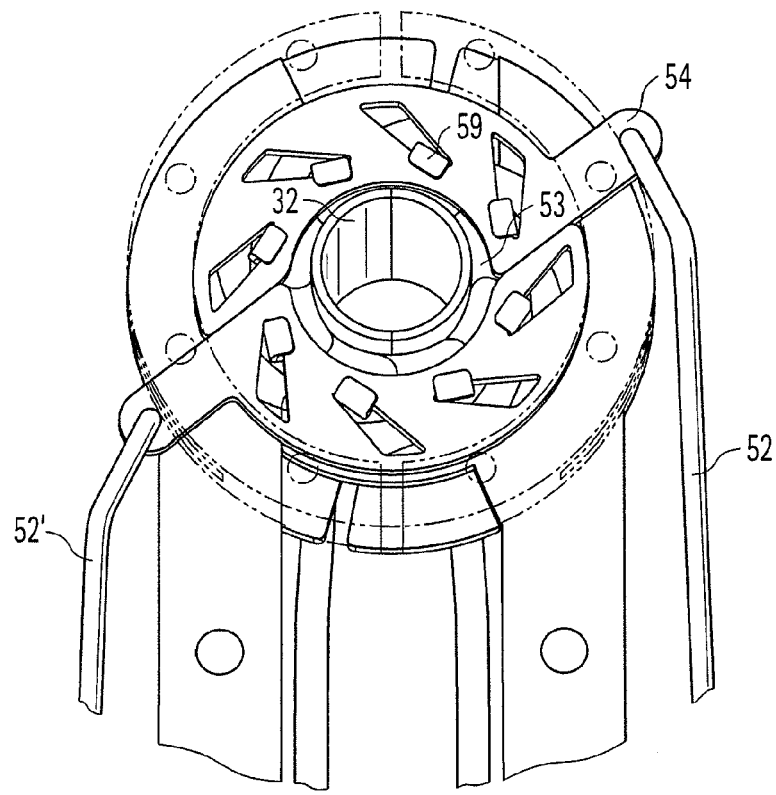
FIG. 8 shows a detailed view of the iris diaphragm of FIG. 1 (iris diaphragm closed)
Figure 9:
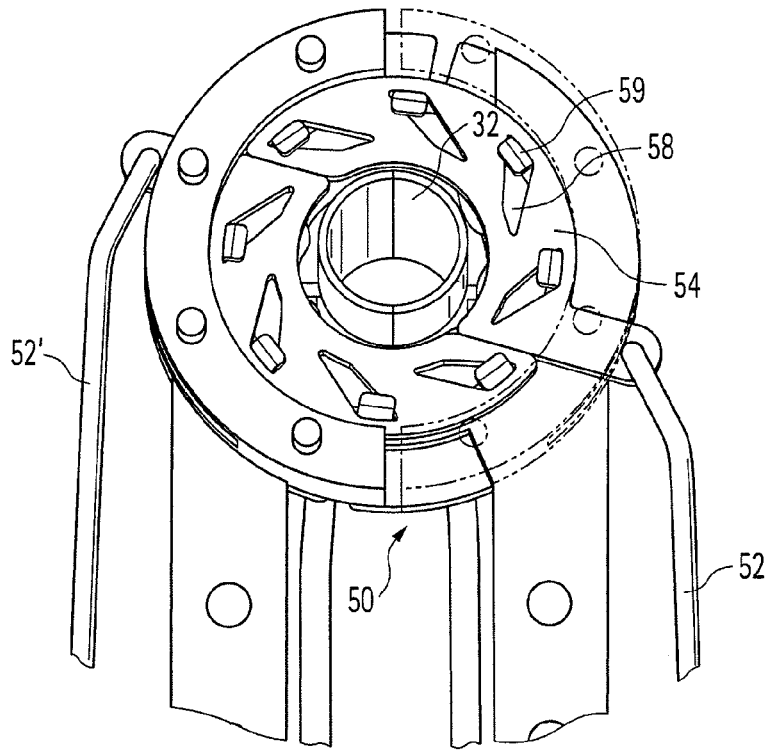
FIG. 9 shows a detailed view of the iris diaphragm of FIG. 1 (iris diaphragm open)

An essential point of the disclosed embodiments lies in constructing the device head of the electrosurgical instrument 10 in the form of a partable iris diaphragm 50. As shown in FIG. 1, the iris diaphragm 50 comprises two half diaphragms 51, 51' which, in the closed state, cooperate as one iris diaphragm 50. The construction of a half diaphragm, specifically the half diaphragm 51, is illustrated in FIG. 6. Said half diaphragm comprises a fastening plate 56, which is substantially semicircular and is firmly connected to the first arm 12. An also semicircular shell 57 extends along the outer edge of said fastening plate 56. The shell 57 has an aperture 60 through which a sickle-shaped actuating plate 54 extends into the interior of the half diaphragm 51. The actuating plate 54 can be actuated by the actuating element 52 such that said actuating plate performs a circular movement about the center of the iris diaphragm 50. Arranged between the actuating plate 54 and the fastening plate 56 is a plurality of lamellae 53, 53', 53", which are partially pivotably connected to the fastening plate 56. Claws 59, 59' on the lamellae 53, 53', 53" engage in corresponding lamellar linkage plates 58 in the actuating plate 54. The lamellae 53, 53', 53" are configured and arranged such that the orientation of the lamellae 53, 53', 53" can be altered by the movement of the actuating plate 54. As FIGS. 8 and 9 show, the lamellae can assume at least two positions. The lamellae 53, 53', 53" have inner walls 66, which act as electrodes. In a first position (FIG. 9), the lamellae 53, 53' are positioned so as to hardly project beyond the actuating plate 54. A circular through aperture, into which the sleeve 32 extends, is formed. Situated between the sleeve 32 and the inner edges 66 of the lamellae 53, 53' is a gap suitable for accommodating sections of the hollow organs.

In a closed position, the through aperture is reduced such that the inner edges 66 of the lamellae 53, 53', 53" lie against the sleeve 32 (see FIG. 8). Insofar as tissue sections of the hollow organs are situated between the inner edges of the lamellae 53, 53', 53" and the sleeve 32, they are pressed against one another and against the sleeve 32 with a defined force. This force can be adjusted with the closing force adjusting device 45 and is transferred via the actuating elements 52, 52' to the lamellae 53, 53', 53".

The covers 55, 55a (FIG. 6) are alternately placed on the half diaphragms 51, 51' to protect their mechanisms.

FIG. 7 shows a further embodiment of the lamellae 53, 53'. Said lamellae are configured stepped and close to each other such that a first lamella 53 not only slides over the second lamella 53', but also engages it.

Figure 10:
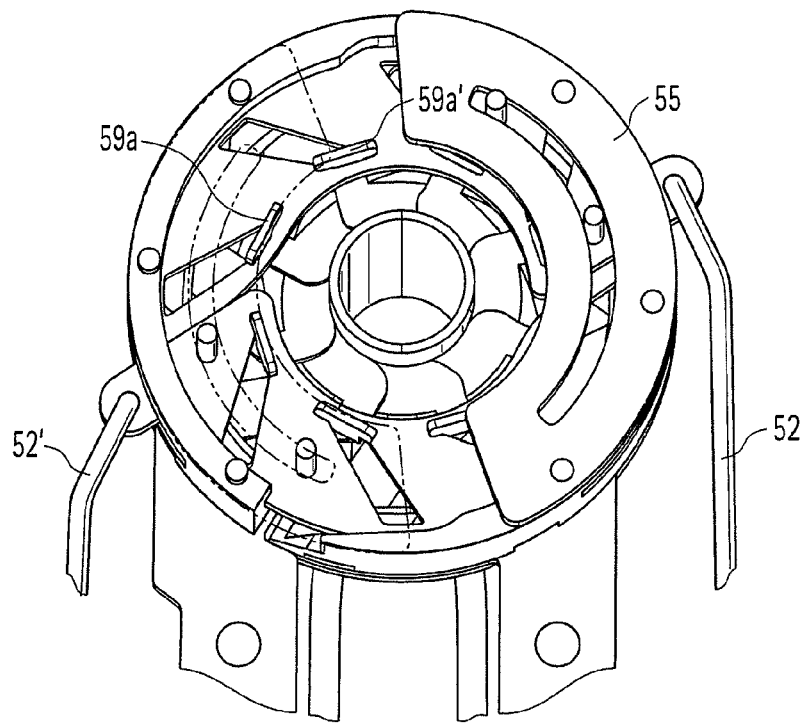
FIG. 10 shows a detailed view of a further embodiment of an iris diaphragm (iris diaphragm closed)
Figure 11:
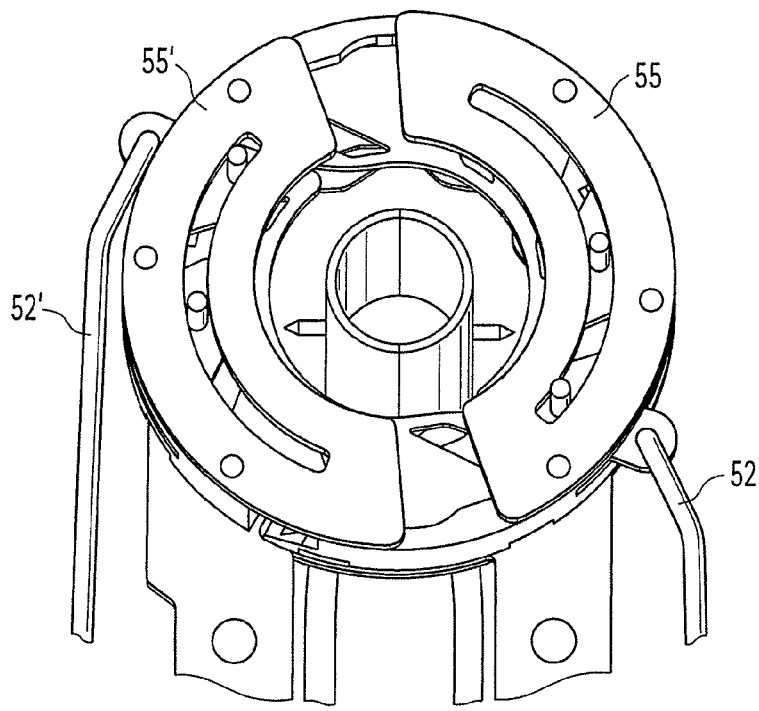
FIG. 11 shows the iris diaphragm of FIG. 10 (iris diaphragm open)

A further embodiment of the lamellae 53, 53' is shown in FIGS. 10 and 11. FIGS. 10 and 11 show the iris diaphragm 50 in a plan view, wherein the iris diaphragm 50 is closed in FIG. 10 and is open in FIG. 11. For the sake of a better view of the mechanism of the iris diaphragm 50, the cover 55' is removed in FIG. 10. It is apparent that the lamellae 53, 53' engage via T-anchors 59a, 59a' in the lamellar linkage plate 58 of the actuating plate 54. The T-anchors 59a, 59a' perform the function of the claws 59, 59'. Pins, which are arranged on the actuating plate 54 of the half diaphragms 51, 51' and engage in the covers 55, 55', form a linkage guide for the actuating plates 54. Said pins guide the actuating plates 54, during the rotational movement thereof, about the center of the iris diaphragm 50, and thus increase the closing range of the lamellae.

Figure 12:
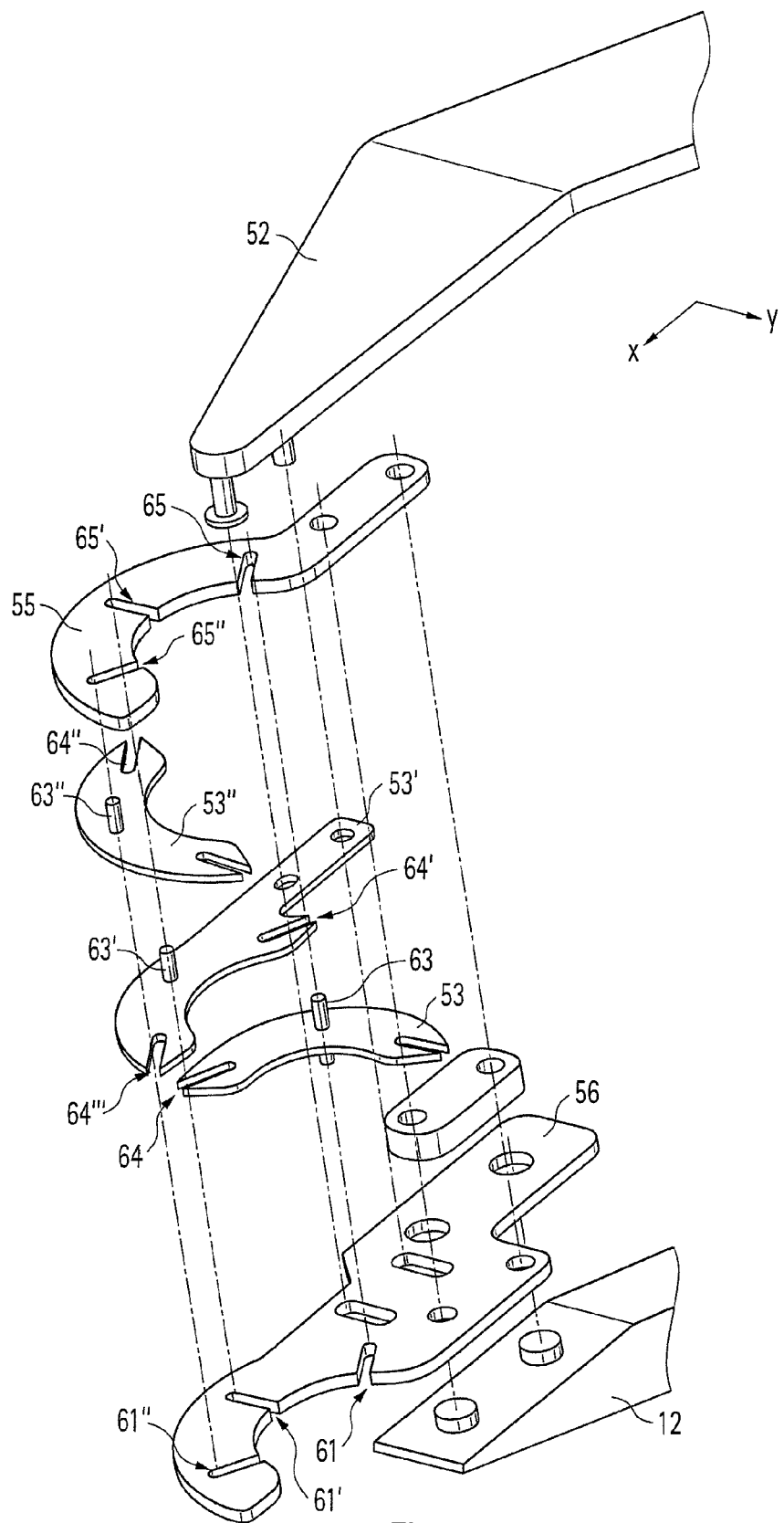
FIG. 12 shows a further embodiment of the iris diaphragm in an exploded view.
Figure 13:
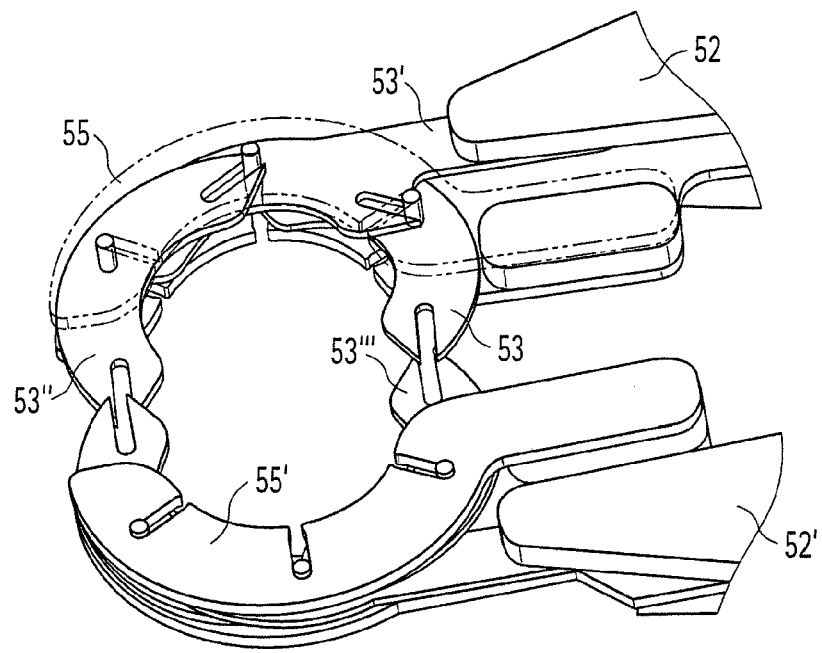
FIGS. 13 and 14 show detailed views of the iris diaphragm of FIG. 12.
Figure 14:
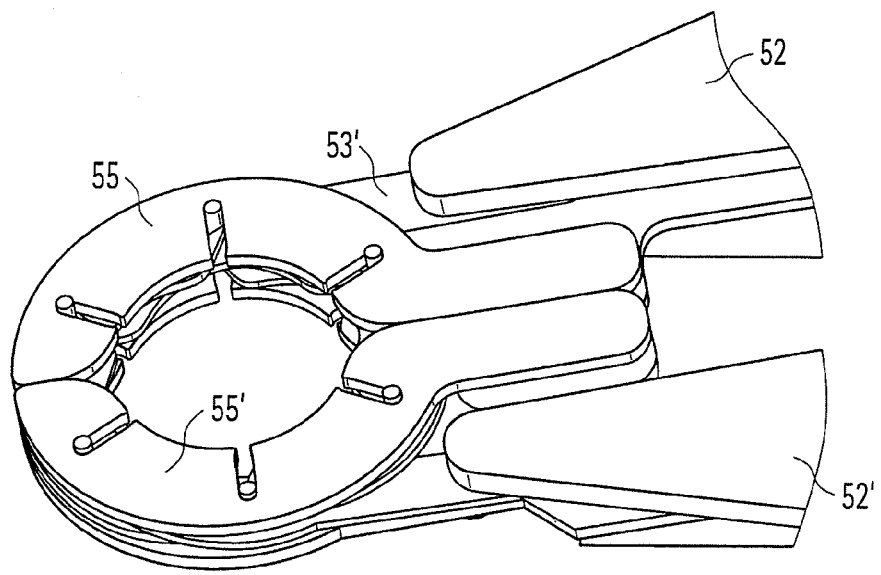

FIGS. 12 to 14 show a further exemplary embodiment of the iris diaphragm 50 having a simpler construction. In order to explain the mechanical processes, a coordinate system will now be introduced. The X-axis of this coordinate system extends substantially along one arm 12. The Y-axis lies transversely thereto and points toward the center of the through aperture of the iris diaphragm 50.

FIG. 12 shows, by way of example, the first half diaphragm 51 in an exploded view. A substantial difference in the exemplary embodiment according to FIGS. 12 to 14 as compared with FIG. 6 is that the function of the actuating plate 54 in the exemplary embodiment of FIGS. 12 to 14 is realized by one of lamella 53 to 53", specifically the lamella 53'. The fastening plate 56 of FIG. 12 is also firmly connected to the first arm 12. Said fastening plate has three cut-outs 61, 61', 61", which open radially in the direction of the center of the through aperture of the iris diaphragm 50. Lamella pins 63, 63', 63" are placed in cut-outs 61, 61', 61". Said pins are arranged substantially centrally on the lamellae 53, 53', 53". The cut-outs 61, 61', 61" form a linkage guide along which the individual lamellae 53, 53', 53" can be moved toward the center of the through aperture. The lamella pins 63, 63', 63" are provided on both sides of the lamellae 53, 53', 53". They engage, on one side, in the cut-outs 61, 61', 61" of the fastening plate 56 and, on the other side of the lamellae 53, 53', 53", in cut-outs 65, 65', 65" of the cover 55. The cut-outs 65, 65', 65" of the covers 55 also extend substantially toward the center of the through aperture of the iris diaphragm 50. Lamella 53' is rigidly connected to the actuating element 52 and has a corresponding projection for this purpose. The actuating element 52 is actuated along the Y-axis. Therefore, by means of the actuating element 52, the second lamella 53' can be moved in the direction toward the center of the through aperture. The semicircular lamellae 53 to 53" each have a cut-out 64, 64', 64", 64''' at their ends, which engage with the pins 63, 63', 63" of the other lamellae 53 to 53". A mechanical coupling is therefore made between the first lamella 53 and the second lamella 53' (cut-outs 64, 64') which, in turn, is connected to the third lamella 53" (cut-outs 64", 64'''). The movement of the second lamella 53' along the Y-axis causes actuation and displacement of the first and third lamellae 53, 53". The linkage guides are configured to move each of the lamellae 53 to 53" toward the center of the through aperture when the second lamella 53' is displaced along the Y-axis. A contrary movement of the second lamella 53' causes this movement to be reversed. The iris diaphragm 50 opens.

The second half diaphragm 51' is correspondingly symmetrically constructed. FIGS. 13 and 14 show the half diaphragms 51, 51'. It is apparent that, in a closed state of the electrosurgical instrument 10, the first lamella 53 of the first half diaphragm 51 enters into a mechanical connection with the lamella 53''' lying opposed thereto. Here also, there is a connection between the lamella pins 63, 63', 63" and the cut-outs 64, 64', 64". The same applies for the third lamella 53".

The coupling of the lamellae 53 to 53" of the first half diaphragm 51 to the lamellae of the second half diaphragm 51' is releasable. In the opened state of the instrument 10, the iris diaphragm 50 has a gap, by which the connected hollow organ can be separated from the instrument 10. Therefore, in the closed state of the electrosurgical instrument 10, a ring of lamellae 53 to 53''' is formed, comprising six lamellae according to the exemplary embodiment of FIGS. 12 to 14. The individual lamellae 53-53''' are each in operative connection with the adjacent lamellae 53-53'''. Taken together, a linkage guide is formed, which enables a translation movement of the individual lamellae 53 to 53''' in the direction toward the center of the through aperture. Actuation of the actuating elements 52, 52' is therefore transferred mechanically to the individual lamellae 53 to 53'''.

Figure 5:
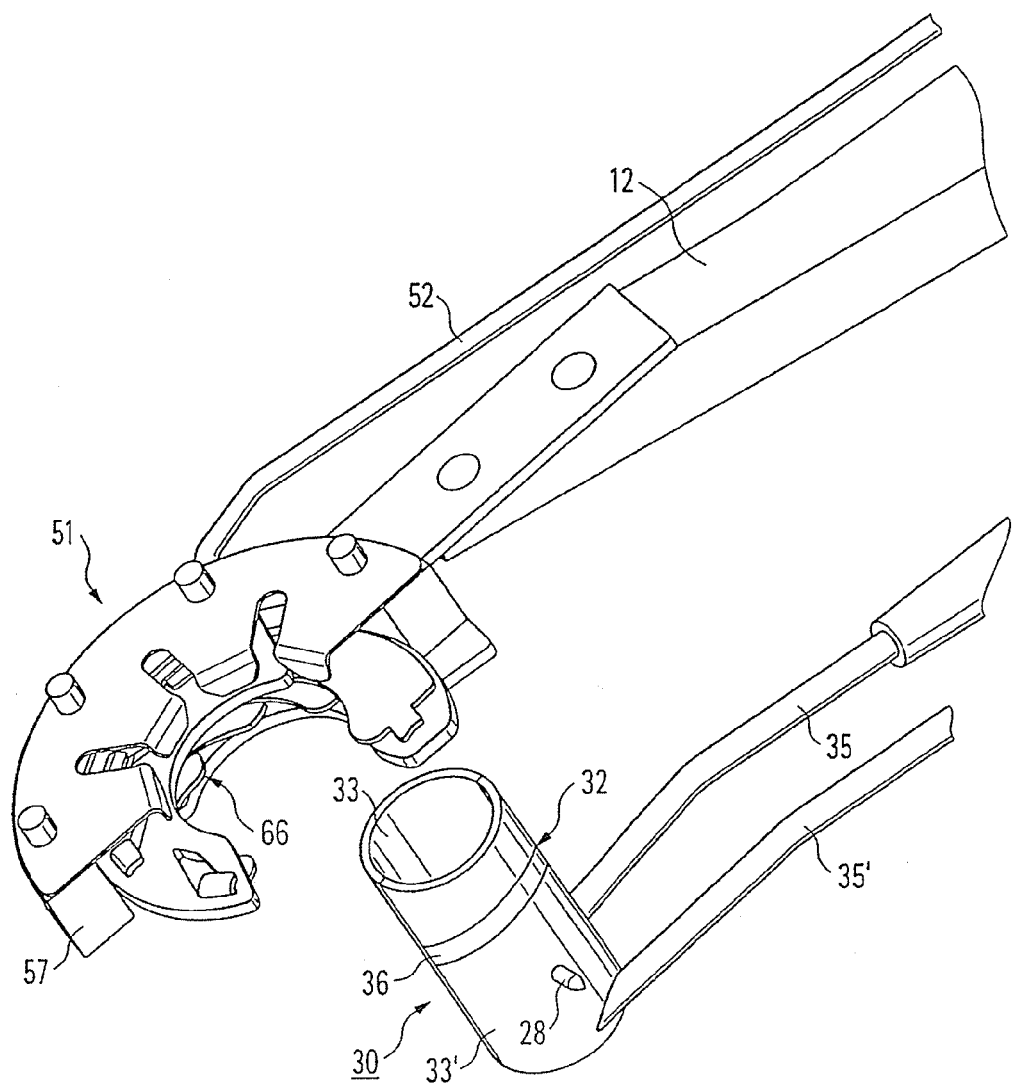
FIG. 5 shows a detailed view of a section of the iris diaphragm of FIG. 1 with a positioning device.

According to the disclosed embodiments, the iris diaphragm 50 comprises a first outer electrode arrangement or outer electrode and the sleeve 32 comprises an inner electrode arrangement, specifically the sleeve electrode 36. As FIG. 5 shows, these electrodes are arranged adjoining one another. The sections of hollow organs clamped between the iris diaphragm 50 and the sleeve 32 can be connected to one another by these electrodes. For this purpose, a corresponding HF current is applied to the electrodes. The HF current causes coagulation of the tissue sections situated between the electrodes. To apply the HF current, the electrosurgical instrument 10 has suitable conductor tracks and terminals. For example, the sleeve electrode 36 can be supplied via a conductor track within the sleeve actuating arms 55, 55'. A suitable conductor track for the iris diaphragm can be situated within the arms 12, 12'.

Alternatively, the arms 12, 12' and/or the sleeve actuating arms 53, 53' can be entirely or partially constructed from electrically conductive material in order to provide a suitable conductor track.

The individual lamellae 53 to 53''' can comprise electrodes for applying the HF current and/or can be made from electrically conductive material.

Preferably, the base plate 13 and the removable section 13' of the base plate 13 is an electrical insulator. Thus, the conductor track of the sleeve electrode 36 is electrically insulated from at least the conductor track of the iris diaphragm 50.

In a further exemplary embodiment, the base plate 13 and/or the removable section 13' can comprise terminals and electrical conductor tracks to supply the electrodes.

Exemplary embodiments with four and eight lamellae 53 to 53'''' have been described. Other embodiments with different amount of lamellae 53 to 53'''' are also conceivable (e.g., with at least four lamellae 53 to 53'''').

The invention claimed is:
1. A device for producing anastomoses between first and second hollow organs, each having inner and outer surfaces, said device comprising:

a sleeve with an inner electrode arrangement, adapted to interface with the first hollow organ such that the inner surface of the first hollow organ is arranged on an outermost surface of the sleeve, and an outer electrode arrangement, which is situated radially opposing the inner electrode arrangement and can be brought into electrical contact with the second hollow organ, which is pushed over the first hollow organ, such that the electrode arrangements make contact with the outer surfaces of the hollow organs, wherein the outer electrode arrangement comprises a plurality of lamellae, which are movable relative to one another by at least one guide member and are configured and arranged such that in a closed state, inner edges of the lamellae form a through aperture and lie against the second hollow organ and, in an open state, a gap is formed between the lamellae, leading from outside to the through aperture, through which the hollow organs connected to one another can be guided outwardly out of the through aperture, and wherein the lamellae are constructed and arranged in the manner of an iris diaphragm to provide a circular opening.

2. The device of claim 1, wherein the sleeve is arranged fixed relative to the outer electrode arrangement in a holder.

3. The device of claim 2, wherein the holder can be removed for individual manipulation of the sleeve.

4. The device of claim 1, wherein in the closed state, all the inner edges of the lamellae are at the same distance from the sleeve.

5. The device of claim 1, wherein the through aperture is adjustable with regard to the diameter thereof by moving the lamellae.

6. The device of claim 1, wherein in the open state, the gap divides the outer electrode arrangement into two sections, which can be moved apart from one another.

7. The device of claim 1, wherein the sleeve is held on an actuating device and is configured to be dismantled into two parts such that the parts can also be brought from a closed state, forming a closed tubular section, to an open state for removal from the hollow organ.

8. The device of claim 7, wherein in the closed state, the actuating device is pre-tensioned.

9. The device of claim 8, wherein the lamellae are pre-tensioned into the closed state with a pre-defined force by a tensioning device.

* * * * *